United States Patent
Pelletier (10) Patent No.: US 10,143,311 B2
(45) Date of Patent: Dec. 4, 2018

(54) KNEE PILLOW

(71) Applicant: Pillow Solve Inc., Montreal (CA)

(72) Inventor: Eileen Pelletier, Montreal (CA)

(73) Assignee: PILLOW SOLVE INC., Montreal, QC (CA)

( * ) Notice: Subject to any disclaimer, the term of this patent is extended or adjusted under 35 U.S.C. 154(b) by 0 days.

(21) Appl. No.: 15/470,052

(22) Filed: Mar. 27, 2017

(65) Prior Publication Data

US 2017/0258238 A1   Sep. 14, 2017

Related U.S. Application Data

(63) Continuation of application No. 14/873,883, filed on Oct. 2, 2015, now Pat. No. 9,603,458.

(30) Foreign Application Priority Data

Oct. 8, 2014   (CA) .................................... 2882016

(51) Int. Cl.
*A47C 20/00* (2006.01)
*A47C 20/02* (2006.01)
*A61G 7/075* (2006.01)
*A61G 7/10* (2006.01)
*A61F 13/06* (2006.01)

(52) U.S. Cl.
CPC .......... *A47C 20/021* (2013.01); *A61F 13/061* (2013.01); *A61F 13/069* (2013.01); *A61G 7/0755* (2013.01); *A61G 7/1096* (2013.01)

(58) Field of Classification Search
CPC ............ A61G 13/1205; A61G 13/1245; A61G 7/065; A61G 7/075; A61G 7/0755; A61G 7/1082; A61G 7/1096; A47C 20/02; A47C 20/021
USPC .... 5/648, 650, 624, 621, 632, 630; 128/845, 128/869, 882, 889, 892; D24/190
See application file for complete search history.

(56) References Cited

U.S. PATENT DOCUMENTS

| | | | | | |
|---|---|---|---|---|---|
| 4,177,806 | A | * | 12/1979 | Griffin | A61F 13/062 128/892 |
| 4,706,302 | A | * | 11/1987 | Padfield | A41D 13/0568 128/882 |
| 4,736,477 | A | * | 4/1988 | Moore | A61F 13/069 128/892 |
| 4,889,109 | A | * | 12/1989 | Gifford | A47C 20/021 5/922 |
| 4,910,818 | A | * | 3/1990 | Grabill | A47C 20/021 297/423.17 |
| 4,926,884 | A | * | 5/1990 | Lonardo | A61F 13/06 128/892 |
| D319,751 | S | * | 9/1991 | Hoff | D6/601 |
| 5,117,522 | A | * | 6/1992 | Everett | A61G 7/0755 5/644 |
| D332,663 | S | * | 1/1993 | Liszewski | D24/190 |
| D333,403 | S | * | 2/1993 | Perrone | D24/190 |
| 5,216,771 | A | * | 6/1993 | Hoff | A47C 20/021 5/490 |

(Continued)

*Primary Examiner* — Robert G Santos
(74) *Attorney, Agent, or Firm* — Anglehart et al.

(57) ABSTRACT

The knee pillow provides sufficient padding above the knee to provide leg spacing and provides padding at the knee to prevent discomforting contact between the medial epicondyle bones and to provide leg alignment for proper posture. The knee cushion is shaped to prevent discomforting displacement of the knee caps (patella).

20 Claims, 7 Drawing Sheets

(56) References Cited

U.S. PATENT DOCUMENTS

| | | | | |
|---|---|---|---|---|
| D342,856 S | * | 1/1994 | Hagen | 5/632 |
| D345,668 S | * | 4/1994 | Braly | D6/596 |
| D348,175 S | * | 6/1994 | Kilbey | D24/190 |
| 5,418,991 A | * | 5/1995 | Shiflett | A47C 20/021 5/647 |
| 5,465,736 A | * | 11/1995 | Lonardo | A61F 13/06 128/889 |
| D366,801 S | * | 2/1996 | Gray | 5/648 |
| D393,073 S | * | 3/1998 | Downing | D24/190 |
| 5,871,457 A | * | 2/1999 | Swedberg | A61F 5/01 128/845 |
| 5,878,453 A | * | 3/1999 | Stokes | A61G 7/0755 5/630 |
| D413,981 S | * | 9/1999 | Swedberg | D24/190 |
| 6,145,508 A | * | 11/2000 | Seip, Jr. | A47C 20/021 128/845 |
| 6,154,905 A | * | 12/2000 | Frydman | A47C 20/021 128/845 |
| 6,182,314 B1 | * | 2/2001 | Frydman | A47C 20/021 128/845 |
| D439,342 S | * | 3/2001 | Seip, Jr. | D24/190 |
| 6,438,779 B1 | * | 8/2002 | Brown | A47C 20/021 128/845 |
| 6,578,218 B2 | * | 6/2003 | Wassilefsky | A61G 7/0755 5/630 |
| 6,640,368 B2 | * | 11/2003 | Roston | A47C 20/021 5/648 |
| 6,807,697 B2 | * | 10/2004 | Druery | A47C 20/021 5/640 |
| 6,954,953 B2 | * | 10/2005 | Bordan | A47C 20/021 128/882 |
| D590,648 S | * | 4/2009 | Rahimian | D6/601 |
| 7,536,735 B1 | * | 5/2009 | Stump | A47C 20/023 5/632 |
| 7,584,516 B1 | * | 9/2009 | Sneed | A47C 20/025 2/23 |
| 7,757,319 B2 | * | 7/2010 | Kimball | A47C 20/021 5/632 |
| 9,603,458 B2 | * | 3/2017 | Pelletier | A47C 20/021 |
| 2001/0027577 A1 | * | 10/2001 | Frydman | A47C 20/021 5/648 |
| 2002/0088057 A1 | * | 7/2002 | Wassilefsky | A61G 7/0755 5/648 |
| 2003/0005521 A1 | * | 1/2003 | Sramek | A47C 20/021 5/648 |
| 2003/0046767 A1 | * | 3/2003 | Roston | A47C 20/021 5/648 |
| 2004/0172761 A1 | * | 9/2004 | Druery | A47C 20/021 5/650 |
| 2005/0000021 A1 | * | 1/2005 | Bordan | A47C 20/021 5/648 |
| 2007/0061973 A1 | * | 3/2007 | Kimball | A47C 20/021 5/632 |
| 2007/0163048 A1 | * | 7/2007 | Kimball | A47C 20/021 5/632 |
| 2008/0092297 A1 | * | 4/2008 | Davis | A47C 20/021 5/648 |
| 2016/0100694 A1 | * | 4/2016 | Pelletier | A61F 13/069 5/648 |
| 2017/0258238 A1 | * | 9/2017 | Pelletier | A61F 13/069 |

* cited by examiner

KNEE PILLOW

This application claims priority of Canadian patent application 2,882,016, filed Oct. 8, 2014, and incorporates by reference US design patent application Ser. No. 29/504,770, filed Oct. 9, 2014.

TECHNICAL FIELD

This application relates to knee pillows or cushions.

BACKGROUND

Using a regular head pillow between the knees is reported to reduce back pain by the Mayo Clinic and many other sources. The use of head pillows between the knees and the use of specially adapted knee pillows are well known, and many different models of adapted knee pillows are commercially available. The general purpose is to provide leg separation at the knee for people sleeping on their sides so as to provide for greater comfort, less joint strain and better circulation than when the knees are allowed to come together.

A loose pillow placed at the knee will fall out of place when a person changes sleeping position from one side to the other. Most adapted knee pillows are contoured to help keep the pillow in position, and some knee pillows are provided with straps for attaching the pillow to a leg. In this way, the pillow may stay on even when the user rolls over in the night.

An example of a contoured pillow that attaches to the leg is U.S. Pat. No. 4,177,806 to Griffin that attaches to one leg both above and below the knee. The pillow is curved to follow a typical sleeping position with the knees slightly bent. Another example of a knee pillow that attaches to the leg, but is not contoured, is described in U.S. Pat. No. 6,145,508 to Seip that attaches both above and below the knee, and provides more rigid foam or padding above and below the knee, while having a flexible batting material at the knee itself so that a user can bend the knee as she wishes during sleep.

SUMMARY

The inventor of the present invention has found that when adequate knee separation is provided by a knee pillow with support at the lower thigh and at the knee provided by adequate contour or compressibility in the pillow, the action of the medial epicondyle bones pushing into the cushion can cause the surrounding rim of the depression to move the knee caps, thus creating discomfort. The knee cap is a sensitive body part, and any sideways pressure or movement on the knee cap is disturbingly uncomfortable and can disrupt sleep.

It has been found by the inventor that the presence of sufficient padding above the knee to provide leg spacing and providing padding at the knee to prevent discomforting contact between the medial epicondyle bones and to provide the basic function of the knee pillow, while being shaped to prevent discomforting displacement of the knee caps (patella), can resolve the problem of discomfort due to knee cap contact. Support at the medial epicondyle bones is important for comfort and furthermore to maintain knee alignment for proper support leg support.

In some embodiments, there is provided a knee cushion for use between a user's legs as the user places one leg over the other during a side-sleeping position, the cushion comprising a first region for contacting lower thighs of a user to provide spacing of the legs during use, a second region for contacting and supporting medial epicondyle bones of knees of the user to prevent discomforting contact pressure at the medial epicondyle bones while maintaining a desired spacing and alignment, with the second region being shaped to prevent a displacement of a knee cap of the user by the cushion during use.

BRIEF DESCRIPTION OF THE DRAWINGS

The invention will be better understood by way of the following detailed description of embodiments of the invention with reference to the appended drawings, in which.

DETAILED DESCRIPTION

Figure 1:
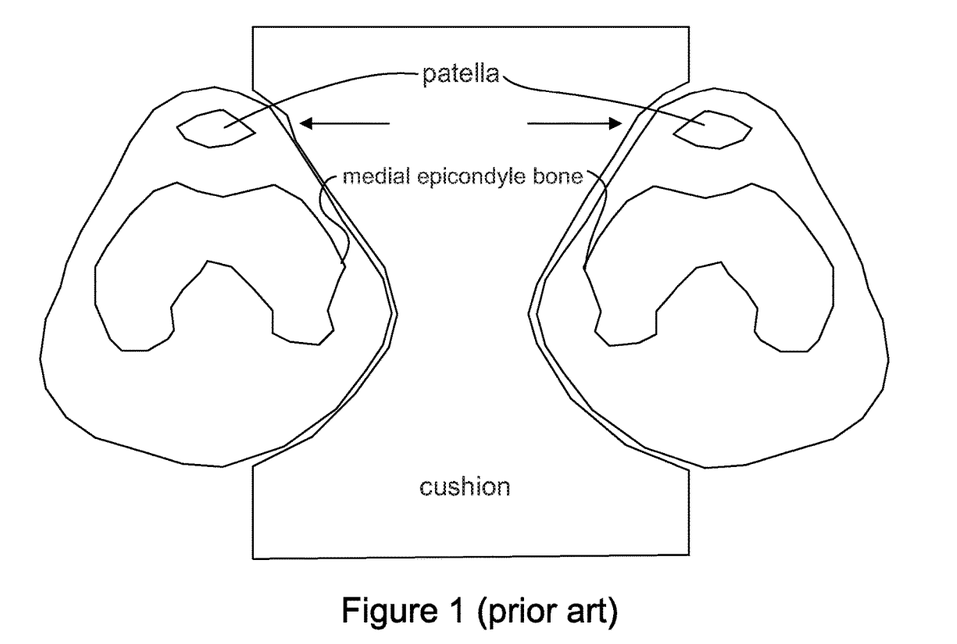
FIG. 1 shows a cross-sectional view of a knees in contact with a knee pillow according to the prior art in which the soft material of the pillow is compressed by the knees with pressure on the knee cap resulting.

To illustrate better the problem of the prior art of a variety of constructions, there is shown a generic cushion placed between the knees in cross-section. As shown in FIG. 1, the medial epicondyle bone region compresses the cushion the most. As the cushion or pillow is made sufficiently thick to provide adequate separation of the legs at the knees, there can be pressure applied to the knee cap or patella region of the knees as schematically illustrated by the arrows. As previously described, such movement of the patella is discomforting to the user. If the cushion is thin enough that there is no pressure on the knee cap, then spacing of the knees can be insufficient for proper spinal or postural support. If the cushion is insufficiently compressible that the knee caps are not disturbed, then the comfort of the knees pressing with their medial epicondyle bones against the cushion can be compromised.

Figure 2:
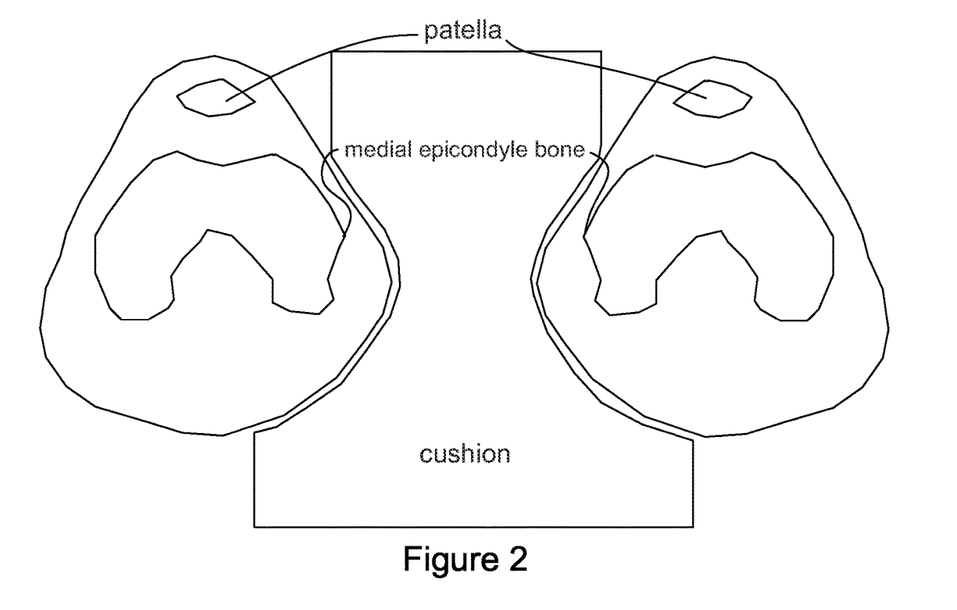
FIG. 2 shows a cross-sectional view similar to FIG. 1 wherein the knee pillow is shaped in the knee region to protect the medial epicondyles while avoiding pressure on the patella.

As illustrated in FIG. 2, the cushion or pillow in the knee region is shaped or structured according to the present invention to avoid pressure on the knee cap area. The shape that will avoid such pressure of the knee region portion of the pillow is a function of both the lower thigh supporting portion and the knee region portion, since more support and separation of the lower thigh can reduce the force applied to the knee region portion of the cushion. However, the knee region portion can be contoured or made of stiffer material, so as to prevent the knee bones from pressing deep enough into the knee region of the cushion such that the knee cap comes into contact with and is thereby moved by the cushion.

As can be seen in FIG. 2, the medial epicondyle bones are anchored within their depressions made in (or contoured in) the cushion. This helps to keep the knees aligned one on top of the other while the user is sleeping within the upper knee and leg slipping forward or backward such that the supper femur twists and exerts poor postural pressure on the spine. While support at the lower thigh (and possibly also the upper tibia) can be useful in helping to maintain this alignment, the solid anchor points of the medial epicondyle bones of the knees are efficient in this function of maintaining alignment.

One embodiment is shown in FIGS. 3 through 7, and is a pillow filled or stuffed with a suitable filling, such as foam pellets or pieces, polyester fiber, polyester pellets, down, etc., with the shape being defined essentially by the containing casing. Such a cushion feels like a pillow and is sufficiently large at the lower thigh to give the desired leg spacing, while providing reduced, but sufficient padding at the medial epicondyle bone region to provide comfort at the knees, while avoiding pressure against the knee caps.

A pillow can also be filled with a pellet material, such as buckwheat, and provide a mouldable and comfortable separation of the legs and support for the knees. A pillow can also be provided with a gel material (e.g. a hydrogel pad) or a high-density foam material as a core, while having a softer foam or pillow material surrounding the core.

Figure 3:
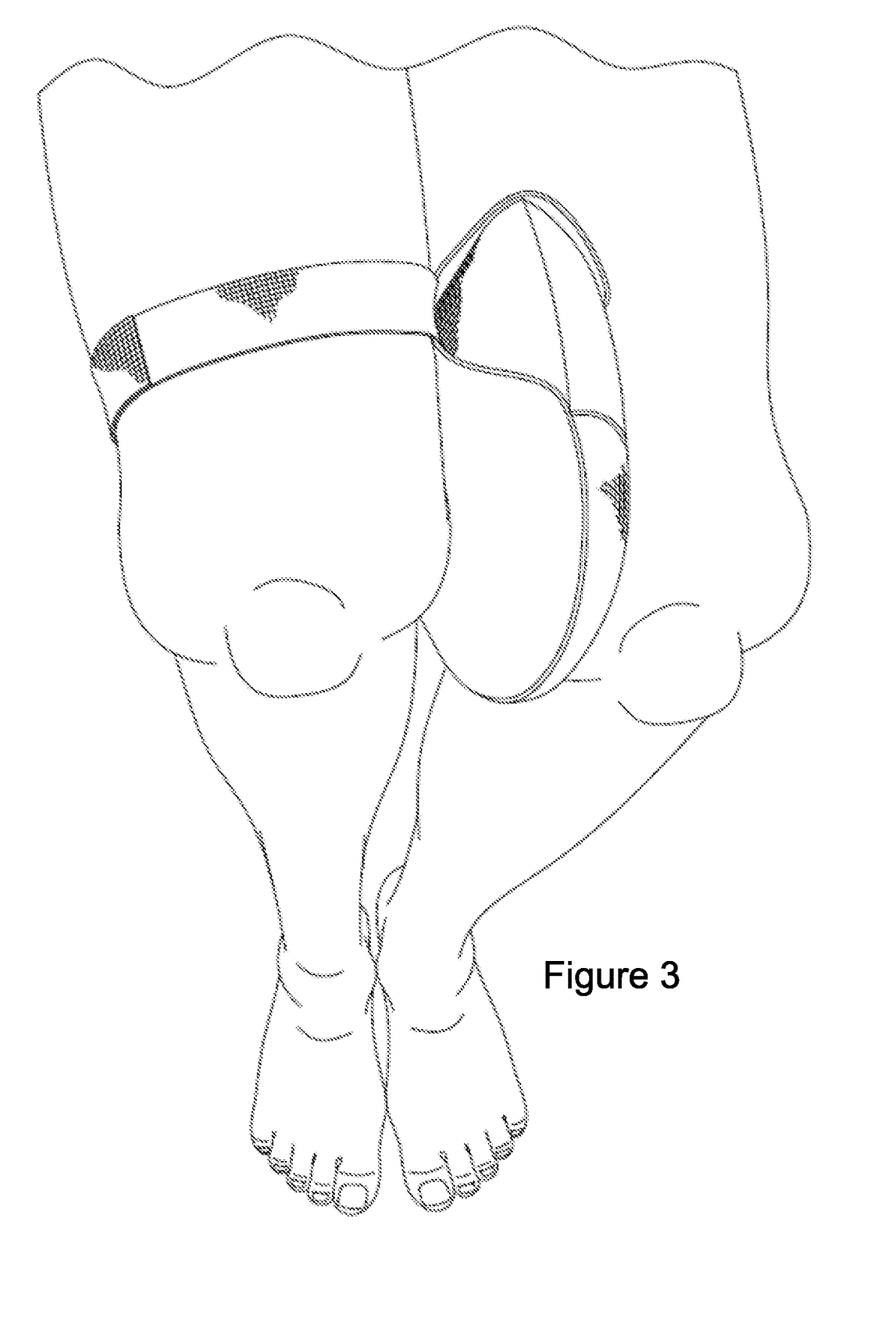
FIG. 3 shows a knee pillow attached by a strap above the knee and placed between a user's legs with the medial epicondyle bones pressing into the pillow while the knee caps are not contacted by the pillow due to the tapered shape of the pillow at the knee area.
Figure 4:
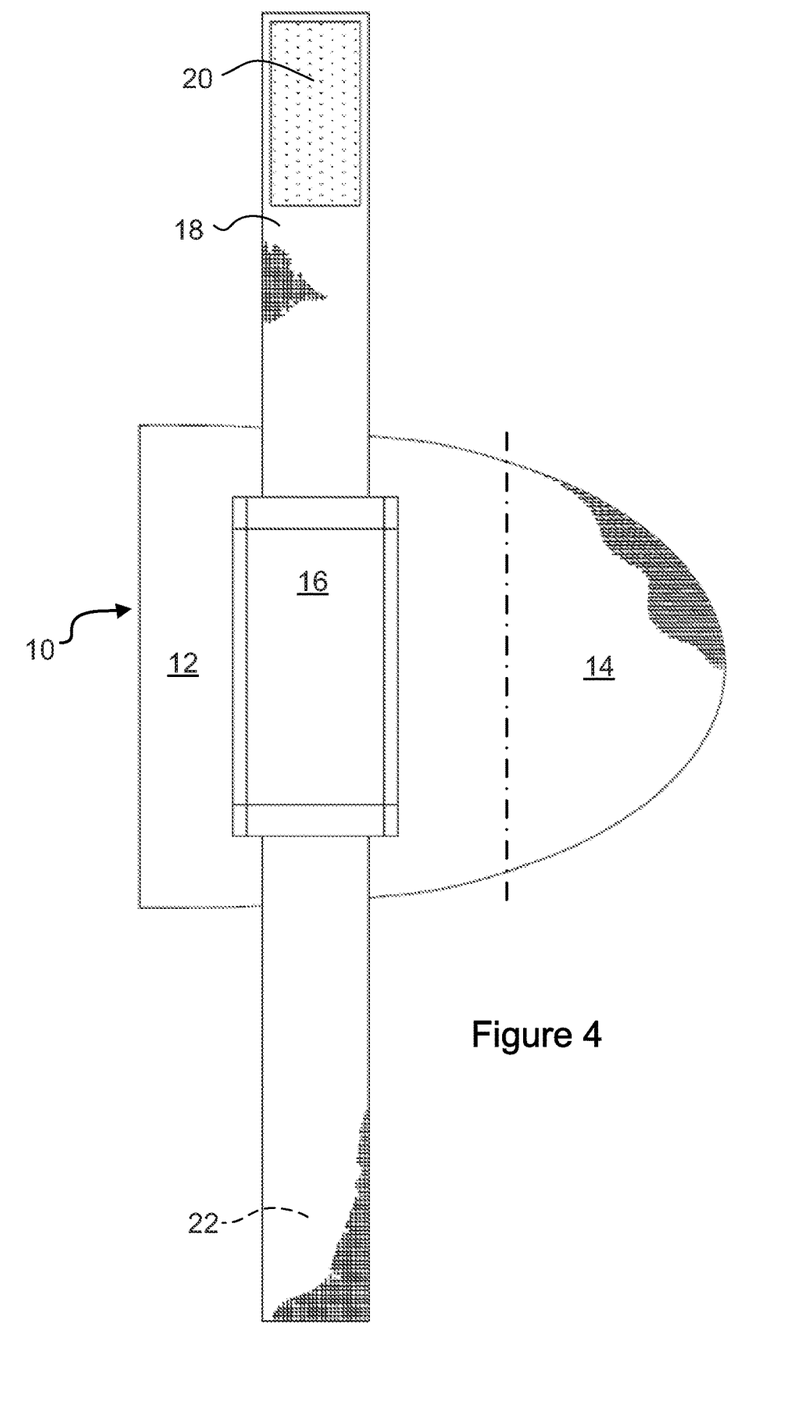
FIG. 4 shows a plan view of the knee pillow of FIG. 1 with its strap and without its cover.
Figure 5:
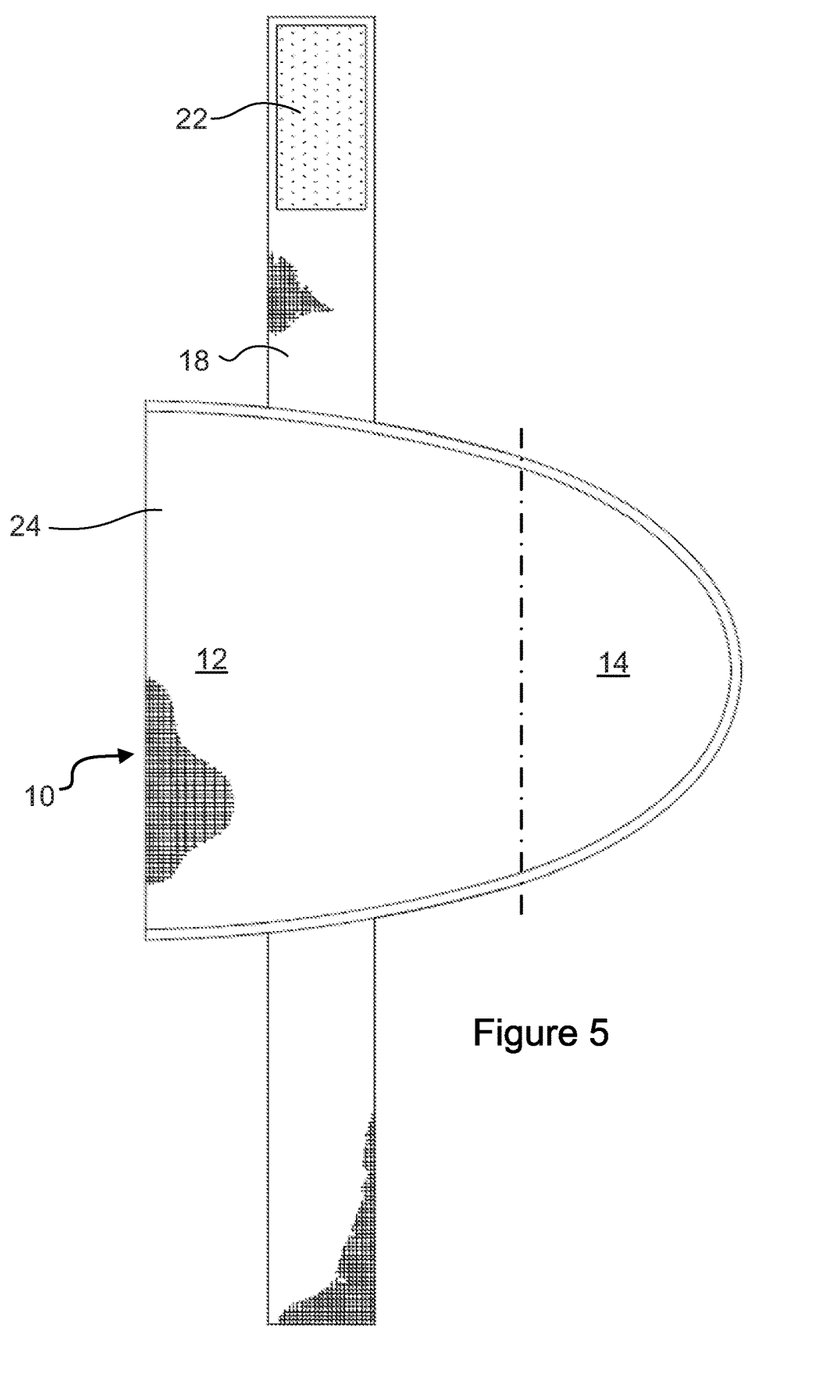
FIG. 5 shows a plan view of the knee pillow of FIG. 4 with its cover.
Figure 6:
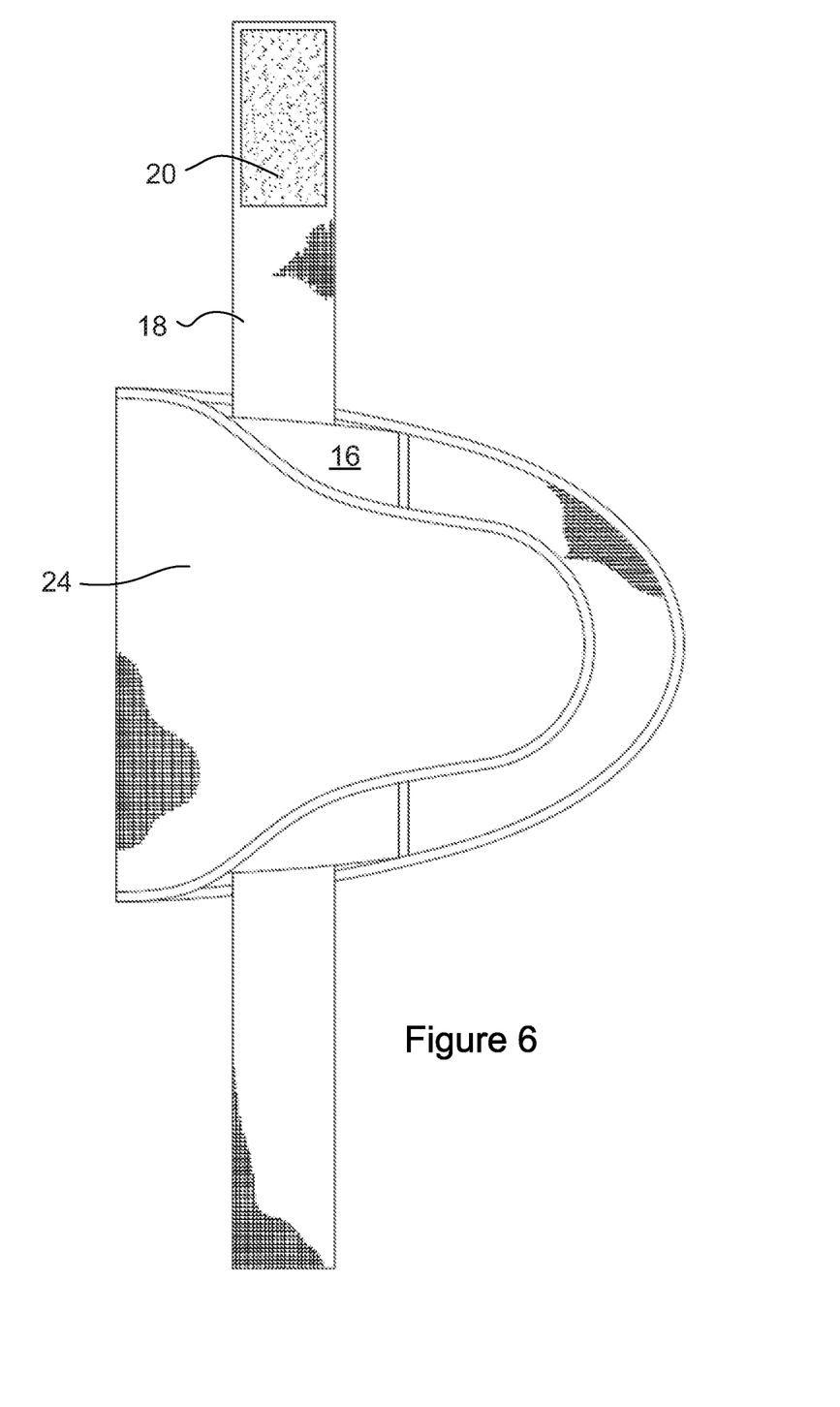
FIG. 6 shows a plan view of the other side of the knee pillow of FIG. 5.

As detailed in FIG. 4, the cushion 10 has a lower thigh engaging portion 12 and a knee engaging portion 14. A loop 16 is attached, for example sewn, onto the casing of pillow 10, through which a strap 18 passes. Velcro™ strips 20, 22 are attached, for example sewn, to the strap 18. FIG. 5 shows the pillow 10 having a washable case 24. FIG. 6 shows the reverse side of FIG. 5 with the flap closure of the case 24 that can be closed using Velcro™ or any suitable fastening mechanism. As shown in FIG. 3, the rounded end 14 of the stuffed pillow 10 provides a tapering of the pillow in both the thickness between the legs or knees and a tapering in width. This reduces the amount of material so that the material does not come into sufficient contact with the knee caps to cause displacement and discomfort.

While the strap shown uses two pieces that attach together on the outside of one leg, it will be understood that the strap can be an elastic loop, for example one covered with loose fabric for comfort, or a loop of Spandex™.

Figure 7:
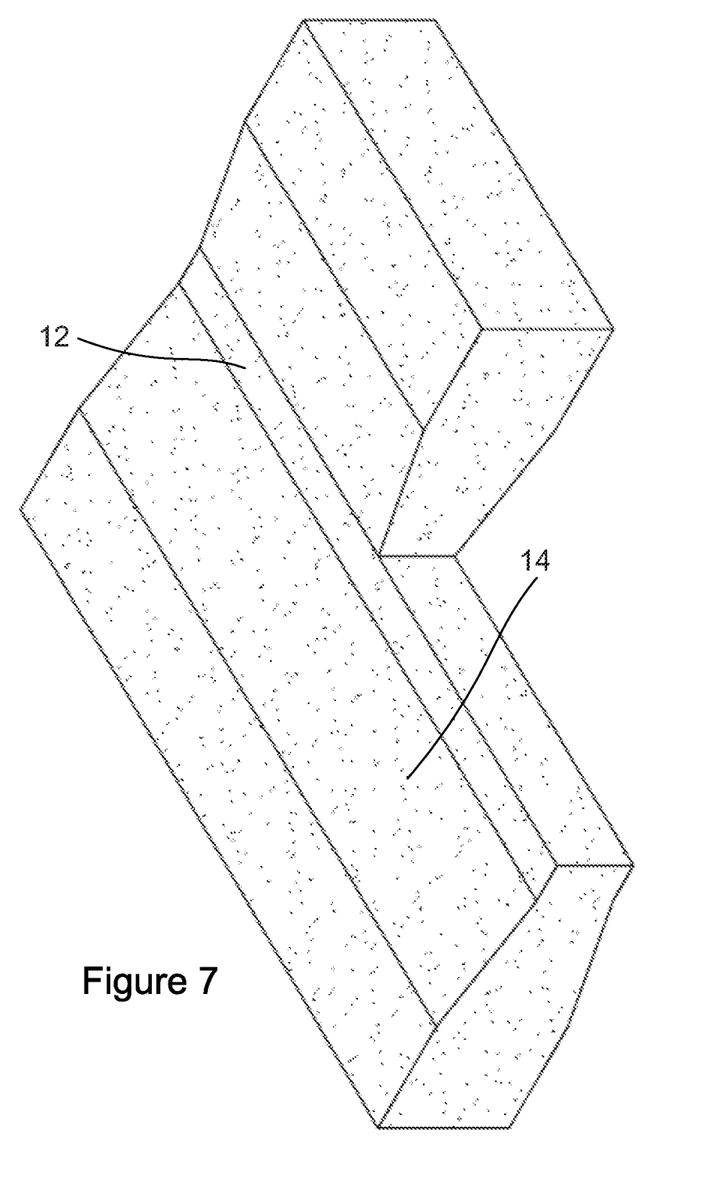
FIG. 7 shows a perspective view of a contoured knee pillow shaped to prevent contact with the knee cap during use.
Figure 8:
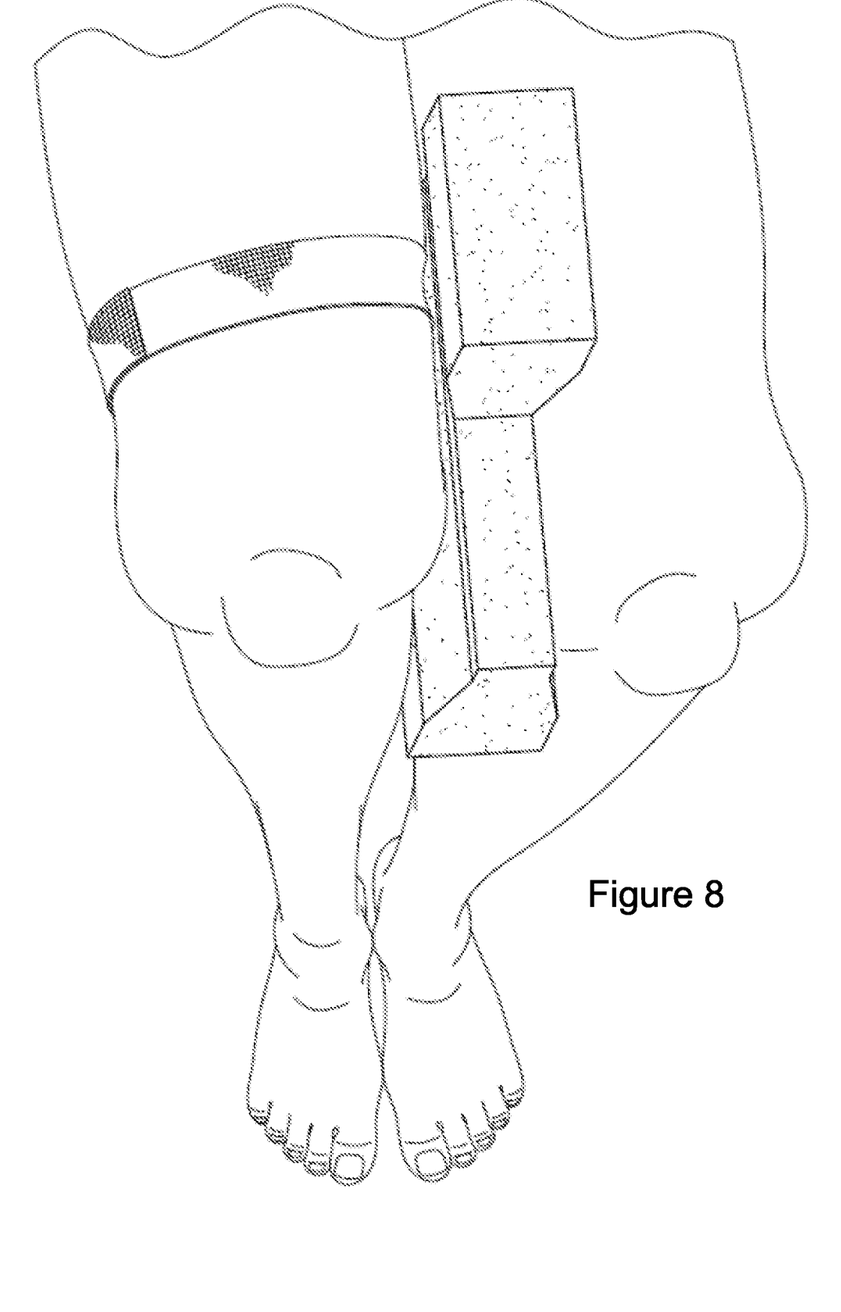
FIG. 8 shows a view similar to FIG. 3 of the knee pillow of FIG. 7 during use.

While the above-described embodiment is a pillow-type cushion that is not contoured to the thigh or knee anatomy, FIG. 7 shows a perspective view of a contoured foam cushion, such as can be made from a memory foam material. Such foam material does not require a casing, although a casing or flocking material can cover the foam. The cushion can also be used with or without a case. A removable case has the advantage of being washable. While a contoured cushion can be used without a strap, a strap offers the advantage of staying with the user when turning from one side to the other. FIG. 8 shows the cushion of FIG. 7 with a strap attached to one leg and placed between the legs similarly to FIG. 3.

The above-described embodiments comprise a cushion having a single portion provide at and above the knee, with no portion provided below the knee as is disclosed by the above-mentioned U.S. Pat. No. 4,177,806 to Griffin and in U.S. Pat. No. 6,145,508 to Seip. It will be appreciated that the shaped knee region according the above embodiments can equally be applied to knee cushions provided with attachments to both above and below the knee.

What is claimed is:

1. A knee cushion for use between a user's two legs in case the user places one leg over another in a side-sleeping position, each of the user's two legs having a thigh portion, an epicondyle portion and a patella portion, the cushion comprising:
    a first region having a width configured to extend across a thigh portion, a variable thickness configured to extend between the two thigh portions, and a first compressibility suitable for contacting the two thigh portions to provide spacing of the two legs when a weight of one leg rests on another leg in said side-sleeping position;
    a second region configured to extend lengthwise from the first region across an epicondyle portion and having a width reduced with respect to the width of the first region, a continuously variable thickness substantially reduced with respect to the thickness of the first region, and a second compressibility suitable for contacting and supporting medial epicondyle bones of the epicondyle portions to prevent discomforting contact pressure by maintaining a desired spacing and alignment, said second region being shaped and said second compressibility being suitable to prevent displacement of a patella portion by the cushion during use as said second region is compressed by an epicondyle portion pressing towards another as a result of one leg-weighing against another leg during said side-sleeping position; and
    an attachment to substantially attach the cushion to one leg for maintaining the first compressible region and the second compressible region in position so that the second compressible region does not press against either patella portion in case the cushion is compressed by the weight of one leg on top of another during said side-sleeping position.

2. The cushion of claim 1, wherein the attachment comprises first and second strap portions attachable to the first region at one end and connectable together at another end.

3. The cushion of claim 1, wherein the cushion has a material-filled casing providing a first width and thickness at said first region and a tapering width and thickness in said second region.

4. The cushion of claim 3, wherein the cushion is filled with a synthetic-fiber filler material.

5. The cushion of claim 3, wherein the cushion is filled with a particulate material.

6. The cushion of claim 1, wherein the second region has an arcuate shape.

7. The cushion of claim 3, wherein the second region has an arcuate shape.

8. The cushion of claim 5, wherein the second region has an arcuate shape.

9. The cushion of claim 1, wherein the first region has a contour configured to support a shape of a lower thigh of the user to prevent sliding of the cushion from between the legs of the user.

10. The cushion of claim 9, wherein the second region is an extension of the first region with a knee cap corresponding side removed or absent.

11. The cushion of claim 9, wherein the cushion is made of memory foam material.

12. The cushion of claim 1, further comprising a removable case.

13. The cushion of claim 1 wherein the attachment comprises at least one of a case, cover, or strap.

14. The cushion of claim 1 wherein the attachment is removable.

15. The cushion of claim 1 wherein the attachment comprises a washable garment.

16. The cushion of claim 1 wherein the attachment comprises at least one of a removable case, cover or washable garment, the attachment further comprising a flap closure configured to contain the cushion.

17. The cushion of claim 1 wherein:
the first region has a shape configured to substantially prevent the cushion from rotating within a case or cover,
the first region has a contour configured to support a shape of the lower thigh of the user to substantially prevent sliding of the cushion from between the legs of the user, and
the second region is an extension of the first region, with a cap portion of the second portion configured to be substantially adjacent to a patella having at least one of increased clearance or greater compressibility than a remainder of the second region.

18. The cushion of claim 1 wherein:
the first region has a substantially polyhedral shape configured to prevent the cushion from rotating within a case, cover or washable garment, and
the second region has a substantially arcuate shape.

19. A method of supporting a user's legs as the user places one leg over the other during a side-sleeping position, the method comprising:
providing a cushion comprising a first region having a width configured to extend across a thigh, a thickness configured to extend between the thighs and a compressibility suitable for contacting lower thighs of a user;
positioning said first region between the thighs to provide spacing of the legs when a weight of one leg rests on another leg during said side-sleeping position;
providing a second region of the cushion substantially continuously tapering from the first region and having a width reduced with respect to the width of the first region for extending across medial epicondyle bones of knees of the user, a thickness reduced with respect to the thickness of the first region and a compressibility suitable for contacting and supporting medial epicondyle bones of knees of the user;
positioning said second region between the medial epicondyle bones to prevent discomforting contact pressure at the medial epicondyle bones to maintain a desired spacing and alignment, said second region being shaped and said compressibility being suitable to prevent a displacement of a knee cap of the user by the cushion as said second region is compressed and deformed by one epicondyle bone pressing against the other as a result of a weight of one leg resting on another leg during said side-sleeping position; and
securing the cushion to one lower thigh of the user for maintaining the first compressible region and the second in position so that the second compressible region does not press against a knee cap of the user as the cushion is compressed by the weight of one leg on top of another during said side-sleeping position.

20. A knee cushion for use between a user's legs as the user places one leg over the other during a side-sleeping position, the cushion comprising:
a first region having a width configured to extend across a thigh, a thickness configured to extend between the thighs and a compressibility suitable for contacting lower thighs of a user;
a first positioning means for positioning said first region between the thighs to provide spacing of the legs when a weight of one leg rests on another leg during said side-sleeping position;
a second region of the cushion substantially continuously tapering from the first region and having a width reduced with respect to the width of the first region for extending across medial epicondyle bones of knees of the user, a thickness reduced with respect to the thickness of the first region and a compressibility suitable for contacting and supporting medial epicondyle bones of knees of the user;
a second positioning means for positioning said second region between the medial epicondyle bones to prevent discomforting contact pressure at the medial epicondyle bones to maintain a desired spacing and alignment, said second region being shaped and said compressibility being suitable to prevent a displacement of a knee cap of the user by the cushion as said second region is compressed and deformed by one epicondyle bone pressing against the other as a result of a weight of one leg resting on another leg during said side-sleeping position; and
a securing means for securing the cushion to a lower thigh of the user for maintaining the first compressible region and the second in position so that the second compressible region does not press against a knee cap of the user as the cushion is compressed by the weight of one leg on top of another during said side-sleeping position.

* * * * *